US005679299A

United States Patent [19]
Gilbert et al.

[11] Patent Number: 5,679,299
[45] Date of Patent: Oct. 21, 1997

[54] METHODS OF MAKING SELF-REINFORCED COMPOSITION OF AMORPHOUS THERMOPLASTICS

[75] Inventors: Jeremy L. Gilbert, Downers Grove; Eugene P. Lautenschlager, Skokie; Richard L. Wixson, Evanston, all of Ill.

[73] Assignee: Northwestern University, Evanston, Ill.

[21] Appl. No.: 612,096

[22] Filed: Mar. 7, 1996

Related U.S. Application Data

[63] Continuation-in-part of Ser. No. 220,242, Mar. 30, 1994, Pat. No. 5,507,814.
[51] Int. Cl.$^6$ ............................. B29C 70/72; D01D 5/12; D01F 1/10
[52] U.S. Cl. .............. 264/103; 156/148; 156/161; 156/167; 156/172; 156/185; 264/210.6; 264/210.8; 264/211.17; 264/257
[58] Field of Search ..................... 264/103, 210.6, 264/210.8, 211.17, 257; 156/148, 161, 167, 172, 185

[56] References Cited

U.S. PATENT DOCUMENTS 4,743,257  5/1988  Tormala et al. ............... 264/257 X

*Primary Examiner*—Leo B. Tentoni
*Attorney, Agent, or Firm*—Tilton Fallon Lungmus

[57] ABSTRACT

Self-reinforced composites of amorphous thermoplastic materials such as poly(methylmethacrylate), polycarbonate and polysulfone are made by melt-extruding and simultaneously drawing and cooling the material to produce fibers with longitudinally-oriented molecular chains, then arranging the fibers in a preform, such as a mat, rod, plate or other useful shape, in which adjacent fibers are in contact with each other, and thereafter heating the preform with fiber constraint to a temperature above the glass transition temperature and below the degradation temperature of the thermoplastic, and applying pressure, to soften and fuse together the outer surfaces of the fibers without completely eliminating the longitudinal orientation of the molecules within the fibers. Where the amorphous thermoplastic is poly(methylmethacrylate), the preform may be wrapped about the bone-implantable element of a joint prosthesis to provide a high-strength integrated mantle of connected, contracted, and oriented fibers. Upon implantation of the element in the intramedullary cavity of a bone, the surface of the self-reinforced mantle of sintered fibers may then bond chemically with a grouting of conventional poly (methylmethacrylate) bone cement.

34 Claims, 3 Drawing Sheets

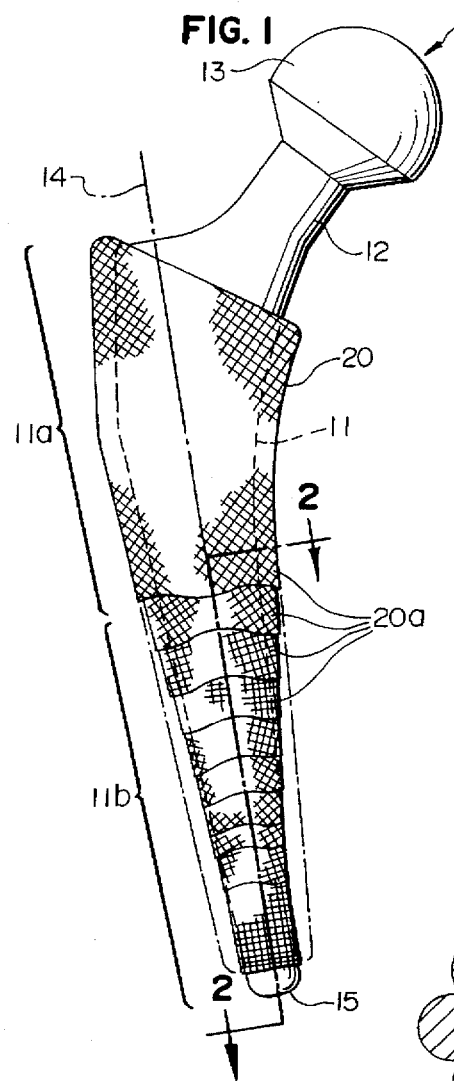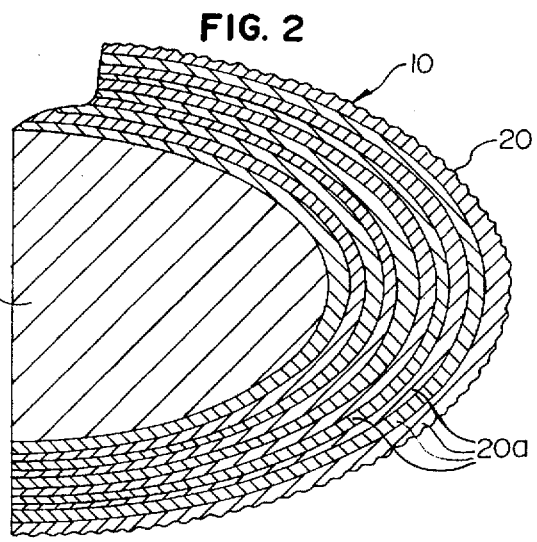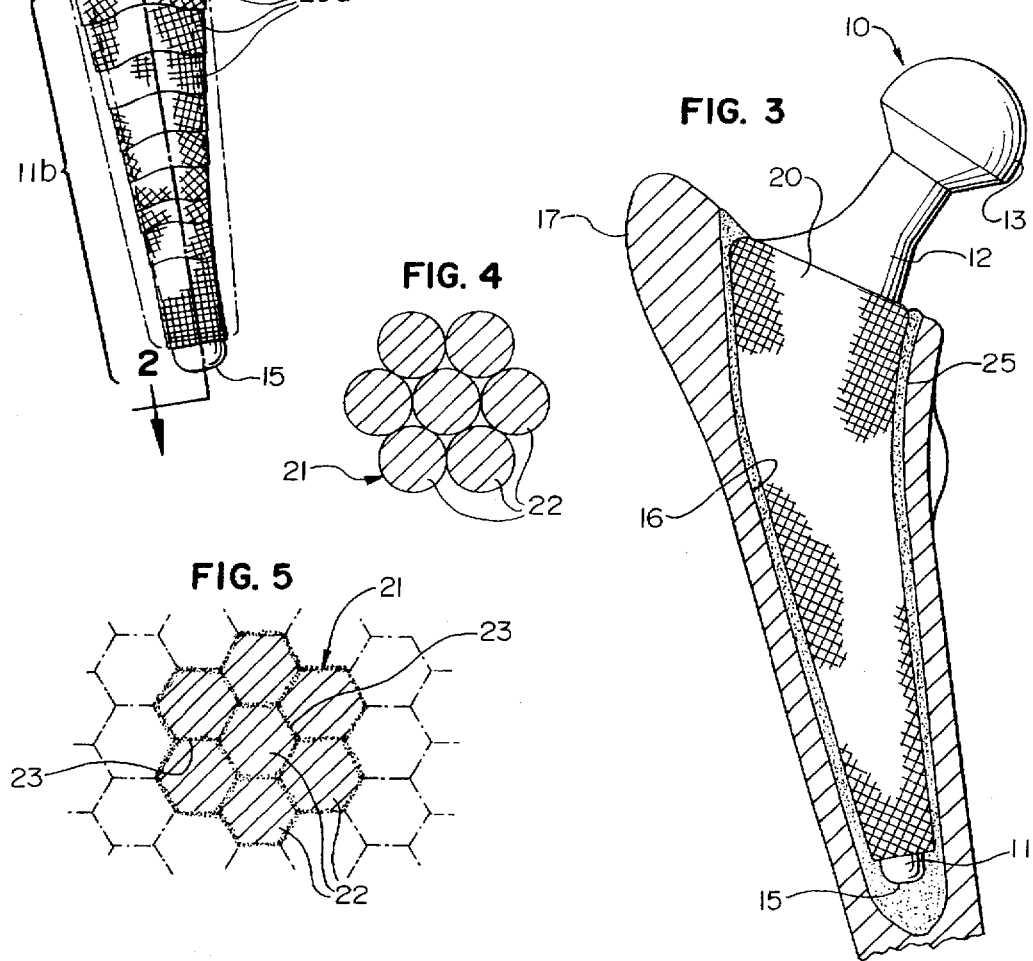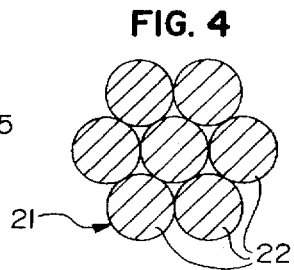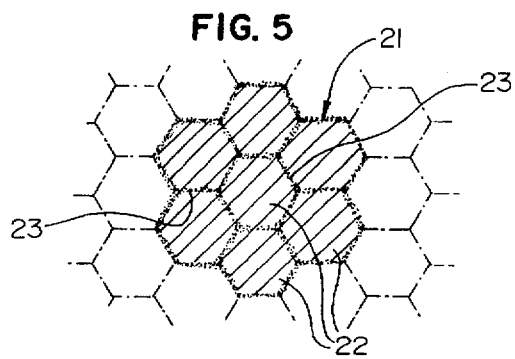

METHODS OF MAKING SELF-REINFORCED COMPOSITION OF AMORPHOUS THERMOPLASTICS

RELATED APPLICATION

This application is a continuation-in-part of our application Ser. No. 08/220,242, filed Mar. 30, 1994, now U.S. Pat. No. 5,507,814.

BACKGROUND AND SUMMARY

This invention is concerned with self-reinforced composites of amorphous (non-crystalline) thermoplastic materials such as poly(methylmethacrylate) (PMMA), polycarbonate (PC), and polysulfone (PS), and to methods of making and using such materials.

PMMA has been widely used in orthopedic surgery as a bone cement and has long been known for its superior biocompatability. In a typical orthopedic implant procedure, PMMA cement is used as a grouting agent to fix the rigid stem (usually metal) of a prosthesis in the intramedullary canal of a bone such as, for example, the femur (as in total hip arthroplasty). PMMA bone cement conventionally includes an acrylic polymeric powder which is mixed in the operating room with a liquid acrylic monomer system to provide a doughy mass. The doughy mass is inserted into the prepared intramedullary cavity and then, while the cementitious mixture is still in a semi-fluid state, the stem of the prosthesis is fitted into the canal. Within a few minutes, polymerization converts the semi-fluid grout into a hardened mantle.

Despite its advantages in terms of biocompatability, PMMA cement is relatively weak (compared to the bone and the implanted stem) and is frequently found unable to withstand the long-term cyclic loading experienced by a prosthetic joint. Over time, fatigue cracking of the cement mantle may occur along with breakdown of the metal-cement interface. Such fatigue cracking may progress to the point at which there is a loss of support of the metal stem in the canal, resulting in the device becoming loose, unstable and painful. The ultimate result may be a need for replacement of the prosthesis, a difficult and painful procedure.

Another limiting aspect of PMMA as an orthopedic cement material is that there are significant drawbacks to having such cement polymerize in the body cavity. Sufficient heat may evolve during the setting reaction to cause tissue damage and necrosis. Also, the monomer itself has been considered toxic and, if it diffuses from the polymerizing mass, local as well as systemic effects can result (including death). During polymerization, there is an associated shrinkage of the PMMA cement of as much as 10% and such shrinkage may cause residual stresses and premature failure of the mantle. Also, during insertion of the prosthetic stem into an intramedullary canal, it is difficult to assure an optimal mantle thickness of about 2 to 4 mm everywhere about the stem and, if substantial variations occur, the non-uniform thickness may accelerate fracture and fragmentation of the mantle.

Some of these problems are discussed in U.S. Pat. No. 4,491,987. In an effort to improve the interfacial bond between the stem of a prosthesis and the bone cement applied at the time of implantation, the patent teaches that the stem, preferably textured or manufactured with a porous outer surface, should be precoated with a thin layer of PMMA. Because of the precoating, a lesser amount of new bone cement is employed during the subsequent surgical procedure. The exotherm of the reaction is thus limited, decreasing the probability of necrosis and reducing the possibility of systemic interference resulting from toxic monomer.

While such a precoat enhances implant-cement interfacial strength by having the new cement bond to the PMMA precoat (instead of directly to the metal or ceramic stem) during implantation, the mechanical properties of the acrylic precoat in terms of strength, modulus, and fracture toughness are not notably superior to those of bulk acrylic.

Considerable effort has been expended to improve the properties of PMMA so that its fatigue behavior more closely matches that of a prosthesis it fixes in place. Some of that effort has involved the reinforcement of PMMA with high strength fibers of stainless steel, carbon, or KEVLAR. See B. M. Fishbane and S. R. Pond, *Clin. Orthop. Rel. Res.*, Vol. 128, p. 194 (1977); R. M. Pilliar and R. Blackwell, *J. Biomed. Mater. Res.*, Vol. 10, p. 893; S. Saha and S. Pal, *Trans. 7th Ann. Soc. Biomater.*, Vol. 4, p. 21 (1981). However, the inclusion of such fibers in a composite bone cement tends to increase the viscosity of the semi-fluid mixture, making application more difficult and increasing the possibility that objectionable voids or windows may occur in the cement mantle. Also, the properties of these composites are controlled by the strength of the fiber-matrix bond which, for the fibers mentioned, is fairly low.

Whether such fibers are incorporated in the acrylic cement applied at the time of surgery or in a precoat applied to the stem of a prosthesis, they introduce an additional material that may create or complicate problems of biocompatability. Such concerns would be reduced if the reinforcing fibers in a PMMA cement matrix were of a like material.

A process for producing higher-strength PMMA fibers for possible use in reinforcing a PMMA matrix has been described in an article by C. A. Buckley, E. P. Lautenschlager and J. L. Gilbert in *J. Applied Polymer Science*, Vol. 44, pp. 1321–1330 (1992), the disclosure of which is incorporated by reference herein. In that process, PMMA was drawn into fibers by melt extrusion followed immediately by a transient temperature drawing process. By adjusting processing variables, fibers ranging from 25 µm to 635 µm in diameter were produced. Those fibers produced by a relatively slow extrusion speed and small extrusion hole diameter combined with a relatively fast draw rate were found to have the highest degree of molecular orientation or alignment as reflected by their relatively high heat relaxation ratios. They were also the fibers of smallest diameter. In fact, molecular orientation was shown to be inversely related to fiber diameter. Both tensile strength (Ultimate Tensile Strength) and modulus increased dramatically with greater molecular orientation, as reflected by length relaxation ratios. For example, a maximum UTS of 225 MPa (megapascals) was observed in a fiber of 36 µm diameter having a length relaxation ratio of 18.7 to 1, representing approximately a 600% increase in strength over bulk PMMA material. More recent data on PMMA fiber processing (unpublished) has shown that the process variables of molecular weight and melt temperature will further influence fiber properties. Specifically, for a fixed weight average molecular weight (212,000 grams per mole) and fiber diameter (30 µm), fiber strength decreases with increasing temperature, where fibers drawn at 210° C. had a strength (UTS) of about 500 MPa (±200 MPa) and those drawn at 260° C. had a strength of 200 MPa (±15 MPa). Similar trends were seen for modulus, 11 GPa (±5 GPa) for 30 µm PMMA fibers drawn at 210° C. versus 5.5 GPa (±1 GPa) for 30 µm fibers drawn at 260° C. However, fiber ductility increased with increasing melt temperature (16%±6% at 210° C. and 31%±7% at 260° C.). Thus, melt temperature during fiber spinning can be used to adjust the resultant self-reinforced PMMA properties. There is a lower limit to melt temperature below which PMMA fibers cannot be spun which depends on molecular weight.

Other references indicating the state of the art are U.S. Pat. Nos. 4,963,151, 4,735,625, 5,037,442, 4,895,573, 3,992,725, 4,718,910, 4,851,004, 5,080,680, 5,180,395, 5,197,990, 4,743,257, 5,171,288, 5,135,804, 4,737,012, 4,403,012, 4,961,647 and 5,415,474.

One aspect of this invention lies in the recognition that while fibers of amorphous thermoplastics having relatively high strength and superior mechanical properties may be produced by melt-extrusion followed by simultaneous drawing and cooling, so that such fibers have longitudinally-oriented molecular chains and a draw ratio, as measured by heat relaxation, of up to 25 to 1 or more and no less than about 3 to 1 (preferably no less than about 6 to 1), the inclusion of such fibers into polymerizing matrix of the same chemical species necessarily fails to utilize, at least to full advantage, the high-strength characteristics of such fibers because, among other things, such fibers are subject to partial or complete dissolution in the monomer used in preparing the matrix. Furthermore, the polymerizing matrix still consists of relatively brittle, low-strength material which limits the overall improvements attainable. This invention involves the further recognition that such problems may be overcome, or greatly reduced, by forming the matrix from the outer layers or strata of the fibers themselves without substantially reducing the longitudinal orientation of the molecules within the fibers. Such fusion is achieved by arranging the fibers in a preform (i.e., an aggregation of fibers), such as a mat, rod, plate or other shape, in which adjacent fibers are in contact with each other and then heating the preform with fiber constraint to a temperature above the glass transition temperature of the amorphous thermoplastic and below its degradation temperature, and applying pressure, to soften and fuse together the outer surfaces of the fibers without complete loss of, and preferably without substantially reducing, the predominant longitudinal orientation of the molecules within those fibers.

Where the amorphous thermoplastic is PMMA, the high-strength fibers and the structure formed from them may be effectively used in the formation of a self-reinforced polymeric mantle encasing the stem of a joint prosthesis, with such fibers retaining their integrity and molecular orientation and with adjacent fibers being interlocked against relative movement.

The PMMA mantle may be formed by wrapping the oriented fibers, or strands composed of a multiplicity (2 to 1000, preferably 20 to 150) of such fibers, in selected directions about the stem of the prosthesis or, alternatively, preforming the fibers or the multi-fiber strands into a mat or sleeve that is wrapped or fitted about the stem at the time of manufacture. In any case, the PMMA fibers extend in controlled directions to form a multi-layered pre-mantle. The pre-mantle is then heated with fiber constraint, and with simultaneously or subsequently applied compressive force, to sinter and interlock the fibers together at their points, lines, or areas of contact without substantially reducing or relieving their molecular orientation, to produce, upon cooling, a textured mantle of connected, contracted, and oriented polymeric fibers about the stem or bone-implantable element of the prosthesis. In that connection, it is to be emphasized that sintering not only locks the PMMA fibers together but, because of limited heat relaxation, causes slight contraction of the fibers and such contraction serves to draw the mantle tightly about the stem. Alternate methods might also use randomly-oriented fibers similarly arranged and constrained, and heated and pressurized, to form a structure of randomly arranged sintered fibers into a self-reinforced composite.

If desired, a PMMA precoat as disclosed in U.S. Pat. No. 4,491,987 may be applied to the stem prior to application of the mantle of self-reinforced molecularly-oriented fibers. In any event, the thickness of the fibrous mantle should be substantial, the average thickness falling within the range of about 1 to 4 mm and preferably 2 to 3 mm, so that a lesser amount of PMMA grout is required at the time of implantation (as compared with conventional practice). The reduced amount of cement required at the time of implantation reduces the exotherm and the incidence of toxic substance to which the body is exposed, while the preformed mantle insures that the stem is enclosed in PMMA and that direct contact between the metallic stem and the intramedullary bone wall does not occur. Since the cement applied at the time of implantation is compositionally identical, or at least chemically bondable, to the fibrous mantle, the monomer of the polymeric mixture used as the grouting material softens and bonds with the outermost stratum of the mantle, thereby integrating the mantle with the applied cement.

The term "PMMA bone cement" is used here to mean a conventional acrylic cement formed from a two component system with one of such components comprising polymethylmethacrylate or methylmethacrylate-styrene copolymer in powder form with barium sulfate radio-opacifier and benzoyl peroxide initiator. The powder is mixed with a liquid monomer, such as methylmethacrylate, which generally also includes activators and inhibitors such as N,N-dimethyl-p-toluidine and hydroquinone, respectively.

It has been found that self-reinforced composites may be produced even where the drawn fibers contain small amounts of finely-divided inert or biologically-compatable additives. In particular, particles of barium sulfate, titanium oxide, zirconium oxide, or other suitable colorant or x-ray opacity-producing agent may be added to the starting polymer melt and, if the particles are sufficiently small (smaller than the ultimate fiber diameter), the fibers may be drawn with minimal loss in desired molecular orientation.

The use of PMMA to produce high-strength self-reinforced composites of sintered or fused fibers is of particular importance because of the biocompatability of such material. While specific examples utilizing the recognized biocompatability of PMMA for orthopedic and dental purposes are disclosed, our methods or processes apply more widely to the production of self-reinforced composites as useful objects in other fields as well, and from other amorphous thermoplastics in addition to PMMA. Thus, where biocompatability for implantation or explantation (dentures, artificial teeth) is not a main consideration, other amorphous thermoplastics, such as polycarbonate (PC) and polysulfone (PSI may be used to form relatively high-strength self-reinforced composites. Such composites may have numerous applications extending well beyond the medical and dental fields, including transparent and non-transparent structural panels and shields; shafts, rods, bars and structures of developed shape for tools, sports equipment, and products of general utility; fiber optic cables and related products, etc. For example, a transparent self-reinforced composite for high-strength optical lenses may be produced by melt-extruding and simultaneously drawing and cooling PC to produce fibers with longitudinally-oriented molecular chains in which each fiber has a diameter within the range of about 5 to about 500 μm and a length heat relaxation ratio of up to 25 to 1 or more and no less than about 3 to 1 in length, then arranging the fibers into a preform or aggregation of fibers in which adjacent fibers are in contact with each other, and then heating the preform for a period of time to a temperature above the glass transition temperature of the PC material and below its degradation temperature while constraining or controlling fiber contraction, and simultaneously or subsequently applying compressive force, to soften and fuse together the outer surfaces of the fibers without destroying the predominant longitudinal orientation of the molecules within such fibers.

DRAWINGS

FIG. 1 is an elevational view of the femoral component of a total hip prosthesis having a preformed self-reinforced fibrous mantle. Certain layers of the mantle are cut away to reveal the multi-layer construction in which fibers, or strands composed of multiple fibers, extend in different selected directions.

FIG. 2 is an enlarged fragmentary cross sectional view taken along line 2—2 of FIG. 1.

FIG. 3 is a partial vertical cross sectional view of the femoral prosthesis in implanted condition.

FIG. 4 is an enlarged fragmentary sectional view of a multiple-fiber strand prior to incorporation in a mantle and constrained sintering thereof.

FIG. 5 is a fragmentary sectional view schematically depicting such strand after mantle incorporation and sintering under pressure.

DETAILED DESCRIPTION OF PREFERRED EMBODIMENTS

Figure 6:
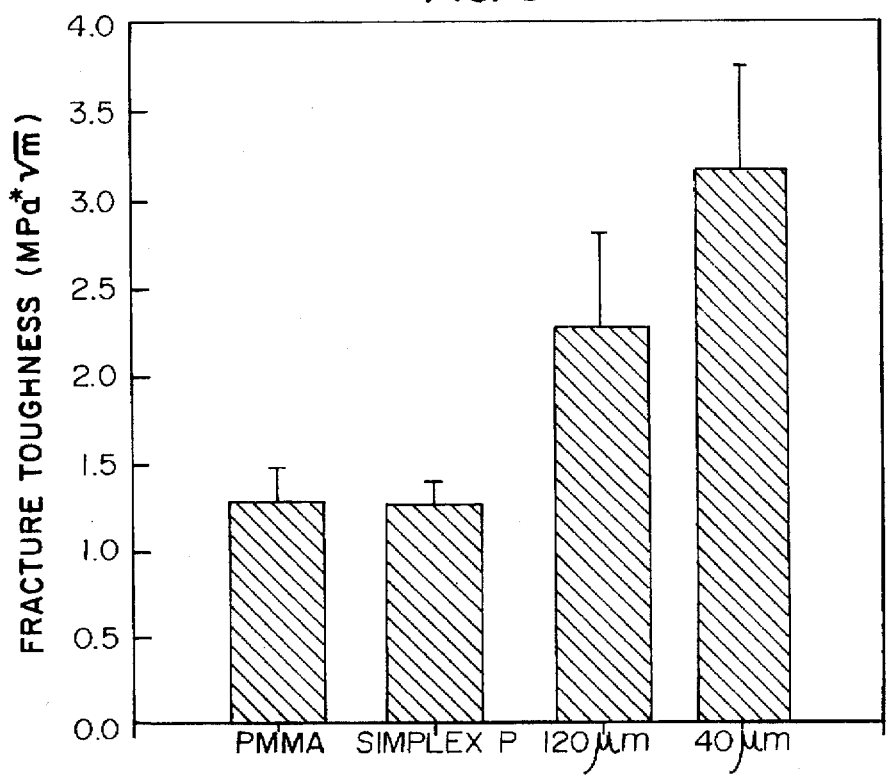
FIG. 6 is a graph depicting the results of fracture toughness tests conducted on samples composed of self-reinforced uni-directional composites prepared in accordance with this invention and compared with samples of bulk PMMA and conventional bone cement.

The processes of this invention are particularly concerned with self-reinforced amorphous thermoplastic composites and products formed from them. Such amorphous thermoplastics include, but are not limited to, poly (methymethacrylate) (PMMA), polycarbonate (PC), and polysulfone (PS). While the processing of these materials to produce self-reinforced composites of improved mechanical properties (strength, modulus, and ductility) have close procedural similarities, operating conditions differ depending on the particular polymer involved. Also, the methods of utilizing such self-reinforced composites may differ markedly. PMMA, for example, is widely known for its biocompatability in orthopedic use, and FIGS. 1–11 are directed to methods of using self-reinforced PMMA composites for producing improved orthopedic implants as well as to basic processing steps of this invention that are applicable to other amorphous thermoplastics and the self-reinforced composites made from them. It should be noted, however, that many other structures and applications may exist for self-reinforced composites made from such polymers and methods.

Referring to the embodiment in FIGS. 1–5, the numeral 10 generally designates the femoral component of a total hip prosthesis having a stem 11, an angular neck portion 12 integral with the stem, and a proximal ball 13. The stem tapers along a primary axis 14 towards a reduced distal end 15 and may generally be considered to include proximal and distal portions 11a and 11b, respectively. As shown in FIG. 3, the stem is dimensioned to be received in the intramedullary canal or cavity 16 of a femur 17. While a femoral implant is depicted for purposes of illustration, it will be understood that this invention is not limited to a hip prosthesis but is applicable to any orthopedic prosthesis, particularly a joint prosthesis, having a rigid stem dimensioned to be received in the intramedullary cavity of a bone. For example, finger, knee, shoulder, ankle and elbow prostheses may benefit from the invention as hereinafter described.

The prosthesis component 11 as so far described is entirely conventional. The particular materials from which the stem, neck, and ball are formed are not critical insofar as the present invention is concerned as long as the prosthesis possesses the requisite strength characteristics. Metal alloys such as stainless steels, titanium and cobalt-chromium alloys are typical and preferred but, if desired, the prosthesis may be fabricated from ceramics or from a combination of metal alloys and polymers such as high-density polyethylene, and the like. The stem of the prosthesis may include a thin PMMA precoating (not shown) applied at the time of manufacture as disclosed in U.S. Pat. No. 4,491,987. As described in that patent, such a prosthesis is preferably manufactured from a chromium-cobalt alloy such as Vitallium with the stem portions of the prosthesis that receive the PMMA precoat being pretreated with sulfuric acid, sandblasting, or the like to prepare fresh, rough, metallic surfaces. If such precoating is omitted, then the surfaces of the metallic stem may be either smooth or roughened.

A preformed self-reinforced composite polymeric mantle 20 encases at least a substantial portion of the length of stem 11. In the illustrated embodiment, the mantle is in the form of a sleeve that extends substantially the full length of the stem; however, other embodiments may include, but are not limited to, only distal coverage, or possibly two spaced locations of coverage—one proximal and the other distal. It is also contemplated that a lesser portion of the stem can be encased by the mantle and, in particular, that only proximal portion 11a of the stem may be so covered while still achieving many if not all of the major advantages described herein.

Mantle 20 is composed of multiple layers of PMMA fibers, such fibers being melt-extruded and simultaneously drawn and cooled to produce longitudinally-oriented molecular chains, all in accordance with the process disclosed in the aforementioned publication by C. A. Buckley, E. P. Lautenschlager, and J. L. Gilbert, *J. Applied Polymer Science*, Vol. 44, pp. 1321–1330 (1992). The fibers should be of a diameter within the range of about 5 to 500 µm and have a draw ratio, as measured by length heat relaxation, of no less than about 3 to 1 and, preferably, no less than about 6 to 1. The degree of length heat relaxation is determined by heating a cut section of a fiber to well above its glass transition temperature (about 110° C.) until the nonequilibrium "frozen in" molecular alignment of the longitudinally-extending polymer chains is released and the chains return to their random coil equilibrium configuration, resulting in a decrease in fiber length and an increase in fiber diameter. Relaxation may be considered complete when the bending and twisting associated with relaxation ceases and the fiber section lays flat and straight for an extended period of time at a temperature above the glass transition temperature. After cooling of the fiber section, the relaxation ratio may then be calculated by measuring the final length of the fiber section and comparing the same with its initial length. The higher the heat relaxation ratio as so developed, the greater the longitudinal orientation of the molecular chains of the fiber prior to testing. While the preferred ratio for the PMMA fibers used in the mantle of this invention is no less than about 6 to 1, higher ratios of 10 to 1 or more are believed particularly desirable.

Acceptable fiber diameters of about 5 to 500 µm define a general range, but a more specific range for achieving the benefits of this invention is 5 to 150 µm, with about 10 to 50 µm being a preferred range. It is believed that the molecular weight of the PMMA may be of an average between 100,000 and 1,000,000, although particularly effective results have been obtained where the average molecular weights fall within the range of about 150,000 to 250,000.

The oriented PMMA fibers used in fabricating the self-reinforced mantle 20 may also be characterized by their relatively high ultimate tensile strength, ductility, and modulus and as compared with unoriented bulk PMMA. In general, such fibers should have ultimate tensile strengths of at least 100 MPa (bulk PMMA of medium molecular weight is of about 25–30 MPa), and preferably at least 200 MPa; percent elongations of at least 3% but up to 40%; and modulus values of at least 2 GPa but up to 15 GPa.

The orientation of the fibers in relation to the stem of the prosthesis is important for effectively resisting the stresses of in-vivo loading. Since the molecular alignment strengthens the fibers in longitudinal directions as well as increases modulus and ductility, a primary objective is that there be an abundance of fibers oriented parallel to the principal stress directions. It has been indicated that with a conventional femoral implant, the stress directions in at least the upper (proximal) portion of the stem are generally in planes normal to the longitudinal axis of that stem. Therefore, while it is believed important to have the fibers of the mantle extend in a plurality of predetermined directions, there should be an abundance of fibers in that portion of the mantle surrounding the proximal portion 11a of the stem that extend in planes that are approximately normal or perpendicular to axis 14. There should also be other fibers extending longitudinally and in other directions in relation to the stem so that when taken as a whole the mantle has fibers extending in a multiplicity of different directions in what might be regarded as "quasi-isotropic" orientation, in contrast to uni-directional orientation. Alternate forms may also be possible, including a random orientation of the fibers.

It is believed that these objectives are most effectively achieved by arranging the fibers into a multi-layered woven mat or fabric extending about the stem of the prosthesis. Because of the small diameter of the fibers, and for other reasons such as ease of application to the stem, it is considered beneficial to weave the layers of the mantle from strands of fibers, each strand containing a multiplicity (2 to 1000, preferably 20 to 150) of such fibers. To illustrate, FIG. 4 shows such a strand 21 (or a portion of a strand) composed of seven PMMA fibers having the mechanical characteristics described. The fibers are shown as being generally uni-directional in each strand but it should be understood that some variations are permissible; for example, the fibers of the strand may be twisted together or one strand may be wrapped about the rest of the strands which remain generally parallel to each other. The strands so formed are then woven to produce a fabric which becomes one layer of the multi-layered mantle. Each layer is arranged so that its fibrous strands extend in predetermined directions with respect to the axis of the mantle to provide the quasi-isotropic orientation mentioned above. If desired, the mantle may be woven into a sleeve upon a mandrel dimensioned to correspond with the size and shape of a prosthetic stem and, when completed, the preformed multi-layered sleeve may be removed from the mandrel and fitted onto the stem into the position shown.

The number of layers should be sufficient to insure quasi-isotropic fiber orientation with particular emphasis on providing an abundance of fibers extending in planes generally parallel with the stress trajectories of in-vivo loading. It is believed that most effective results are obtained if the number of such layers is in the range of 5 to 15. In the embodiment illustrated, mantle 20 is shown to be composed of 10 such layers or strata 20a, but a greater or smaller number may be provided as long as the reinforcing effect of the preformed mantle is not compromised and the average thickness of the resulting multi-layered mantle is 1 to 4 mm, and preferably about 2 to 3 mm.

Completion of the mantle is not achieved until the fibers are locked together in partially contracted condition by a sintering operation. The term "sintering" is used here to include diffusion bonding; that is, adjacent fibers may become fused together along their length or at points of intersection either as a result of the incipient melting of their outer surfaces or by intermolecular diffusion resulting from such heat treatment. The sintering results only in a molecular relaxation of the outer surface of each fiber without substantially reducing the molecular orientation or alignment throughout the body or core of each fiber. Some limited longitudinal contractions of each fiber necessarily occurs but the effect is advantageous because it draws the fibers, strands and successive layers of the mantle into tight interlocking engagement with each other and into firm contractive engagement with the stem about which the mantle extends.

FIG. 5 schematically illustrates the effect of sintering upon a strand 21 of seven fibers 22, the arrangement of fibers being the same as previously described in connection with FIG. 4. Because of peripheral heat relaxation and pressure, each fiber, originally of circular cross section, assumes a hexagonal (or polygonal) configuration with the surfaces of adjacent fibers being fused together as indicated at 23.

The sintering conditions may be varied to achieve maximum fiber-to-fiber bonding with maximum retained molecular orientation, but it has been found that such sintering should include the application of pressure to what may be referred to as an unsintered pre-mantle. The heating and pressurizing steps may be performed simultaneously or in stages, with the latter being preferred because it is believed to be more amenable to lower production times and greater control over retention of molecular orientation.

If the heating and pressurizing steps are to be performed simultaneously, the unsintered pre-mantle about stem 11 may be compressed between two (or more) heated mold sections or by vacuum bagging and heating the stem and pre-mantle in an autoclave. In either case, the sintering should occur at temperatures within the range of about 110° to 180° C. (preferably 120° to 160° C.) for periods of 1 to 90 minutes (preferably 5 to 40 minutes) and at gauge pressures of about 1 to 10 atmospheres, or 0.09 MPa to 0.9 MPa (preferably about 8 to 9 atmospheres).

On the other hand, if the heating and pressurizing steps are to be carried out sequentially, the unsintered pre-mantle is first heated upon the stem by induction or by any other suitable heating technique. For example, the stem with its unsintered pre-mantle may be placed in a furnace at a temperature within the range of about 110° to 180° C. for a relatively short interval of about 1 to 10 minutes until the pre-mantle contracts into tighter engagement with the stem (which serves to constrain and limit such contracting). The stem with its partially sintered pre-mantle is then removed from the furnace and compressed between pre-heated mold sections to complete the sintering operation. The duration of the compression step may vary depending on mantle thickness, mold temperature (in the range of about 110° to 180° C.) and other factors, but generally will fall within the range of about 1 to 30 minutes. Because of the reduced processing times required to achieve complete sintering or bonding of the fibers, this two-step procedure is believed to yield a greater extent of retained molecular orientation for the same level of consolidation.

While the application of pressure to the pre-mantle may be achieved by molding or vacuum bagging as described, it may also be self-induced without requiring additional pressurizing means. For example, it has been found that where the outermost fibers or strands extend generally circumferentially, as where they are wrapped in spiral formation about the underlying fibers or strands of the pre-mantle (or preform), and if the ends of the outermost fibers where strands are restrained against longitudinal contraction, then upon heating to sintering temperatures, the fibers of the outer layer will nevertheless contract into forceful contact with the underlying layer or layers, forming a tight wrapping that effectively self-pressurizes the composite.

The final result, following sintering and compressing procedures (either by externally-applied compressive force, or self-induced compressive force, or both) and subsequent cooling, is an integrated self-reinforced mantle of high-strength oriented PMMA fibers that are contracted, interconnected, and tightly encasing the stem of the prosthesis. Because the strands of fibers are interwoven, the outer surface of the mantle is textured as indicated in FIG. 2. It may also be slightly porous, depending on the sizes of the strands, the closeness of the weave, and the conditions of sintering.

Mantle 20 is a true mantle because of its substantial thickness (in contrast to a precoat) and because it may interface directly with the intramedullary surface of the bone into which it is received. If the prosthesis is to be implanted without bone cement, it is desirable that the mantle's outer surface not only be textured but also porous, thereby promoting bone ingrowth. Preferably, however, the intramedullary canal is reamed and prepared to be slightly larger than the mantle-equipped prosthesis to accommodate a layer of bone cement applied at the time of implantation. Such a layer is designated by numeral 25 in FIG. 3. Because the mantle is compositionally the same as, or is at least chemically bondable to, the applied PMMA cement, a secure bond occurs between the thin layer of grouting cement and the preformed mantle. Since a relatively small amount of cement 25 is required, the exotherm of the reaction is lessened, decreasing the possibility of tissue necrosis and reducing polymerization shrinkage, and a minimal amount of toxic monomer is involved. Such monomer nevertheless constitutes a solvent for the fibrous mantle and, consequently, an outer layer or strata of the mantle becomes chemically bonded to the PMMA cement grouting as that grouting polymerizes.

The PMMA cement applied at the time of implantation may be any approved, self-curing, PMMA bone cement composition. One such composition is marketed by Howmedica, Inc., Rutherford, N.J., under the designation "Simplex-P" and is a two-component system which includes a powder (16.7% PMMA and 83.3% methylmethacrylate-styrene copolymer) and a liquid consisting primarily of methylmethacrylate monomer. Another approved self-curing bone cement is marketed by Zimmer U.S.A., Warsaw, Ind. and is also a two-component system in which the powder component is over 99% PMMA and the liquid component is primarily methylmethacrylate monomer.

Self-reinforced composites of other amorphous thermoplastic materials, such as polycarbonate (PC) and polysulfone (PS), may be made by the same processing steps of melt-extrusion, simultaneous drawing and cooling of fibers, and arranging, constraining, and sintering the fibers, as described above for PMMA. For PC, the processing settings (time, temperature and pressure) may be similar to PMMA, but not necessarily the same. For PS, higher processing temperatures are required because of its higher glass transition temperature (190° C.). Composites of PS may be made at a nominal temperature for sintering of 190° C. or higher. In any event, amorphous thermoplastic self-reinforced composites require drawn fibers of high molecular orientation, arranging fibers, constraining them and heating them to a temperature above their glass transition temperatures for periods of time sufficient to cause sintering without complete loss of molecular orientation.

It is to be noted that if the amorphous thermoplastic used as the starting material is clear, then the self-reinforced composite resulting from the process of this invention may also be clear or transparent. Thus, if self-reinforced PC is used for optical lenses, such lenses will be clear while having superior strength and other physical properties.

It has also been found that coloring agents, or agents to produce x-ray opacity, may be included in the starting material without appreciably reducing the advantages resulting from molecular orientation in the final self-reinforced composite. For example, fibers of PMMA may be extruded with small particle additions (approximately 5 to 10%) barium sulfate having a particle size of approximately 1 to 15 µm. As long as the particles are smaller than the fiber diameter to be drawn, and are uniformly dispersed, the additive has no appreciable effect on the processing steps. As with bone cement, the addition of barium sulfate results in x-ray opacity and may also be useful simply as a colorant. Other particulate agents might also be used as additives, such as titanium oxide, zirconium oxide, etc.

In the embodiment of FIGS. 1–5, where a self-reinforced composite of oriented PMMA fibers is formed about the stem of an implant, the stem serves as a mandrel and, along with the pressure exerted by the mold sections, constrains the fibers and limits their longitudinal contraction during the sintering operation. It is to be understood that the same result may be achieved if the implant were omitted and the composite were instead clamped between two (or more) heated mold sections, or otherwise suitably constrained. Thus, self-reinforced composites of amorphous thermoplastic materials such as PMMA, PC and PS may be made from molecularly-oriented fibers or strands which are arranged in the form of a mat, plate, rod, or other suitable preform, with adjacent fibers in contact with each other and constrained against retraction, and are then heated under pressure to a temperature above the glass transition temperature of the material and below its degradation temperature for a period of time to soften and fuse together the outer surfaces of the fibers without substantially reducing or eliminating the longitudinal orientation of the molecules of those fibers. The heating and pressurizing steps may be performed simultaneously or, as already described, may be sequential, at least in part. In a sequential operation, the fibers of the preform would be supported by a suitable jig or clamp to limit shrinkage and heated for a limited period of time in an oven at a temperature above the glass transition temperature. The preform is then removed from the oven, clamped between heated dies at controlled temperature and for a limited time, and then cooled.

Figure 8:
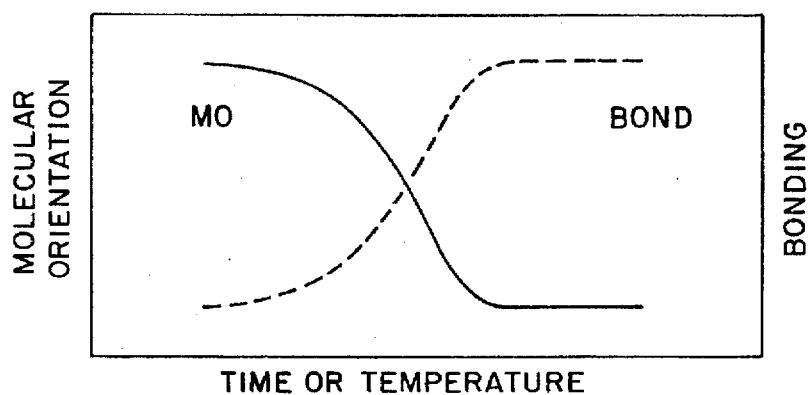
FIG. 8 is a graph schematically illustrating the effects of time and temperature on the molecular orientation and the extent of sintering or bonding in a method of forming self-reinforced composites according to this invention.

During such processing, two competing mechanisms are active which affect the resultant properties of the composite. First, the polymer at the outer surface of a fiber undergoes entanglement with the polymer of adjacent fibers, resulting in a bonding of the fibers. The extent of the bonding is dependent on the pressure, temperature and time (as well as the composition, molecular weight, and degree of orientation of the amorphous thermoplastic material of the fibers). For a fixed temperature and pressure, increasing the time of the sintering treatment results in increasing the extent of bonding. Second, there is a progressive loss of molecular orientation within the fibers as the oriented polymer chains undergo thermally activated motion and attempt to return to their high entropy random state configuration. Even though there is a geometric constraint resulting from the clamping effect of the die sections, the molecular chains will slide past one another and eventually all molecular orientation will be lost. A graphic representation of the two competing mechanisms is shown in FIG. 8 which schematically plots extent of molecular orientation and extent of bonding against either time (at constant temperature and pressure) or temperature (at constant time and pressure).

As indicated in the graph, molecular orientation diminishes as time or temperature (or both) increase. At the same time, the extent of bonding or fusing of the fibers increases with time or temperature or both. The intersection of the two lines of this schematic diagram represents what might be regarded as the optimum, either in terms of time or temperature (whichever is plotted) because it occurs in a region where molecular orientation is retained at the same time that substantial bonding is achieved.

Both the bonding process and the molecular orientation loss process are time, temperature and pressure dependent. For example, for a fixed pressure and temperature, longer times will result in greater bonding but also greater loss in molecular orientation. Pressure will effect this process if it is insufficient to cause the fibers to polygonize (FIG. 5) and contact adjacent fibers. It has been found that woven composites can be fabricated with an applied pressure of about 0.8 MPa; however, a large range of applied pressures is believed to be effective as long as the pressure is sufficient to cause the fibers to condense and contact one another.

Optimal processing occurs when the amount of bonding is maximized while the loss of molecular orientation is minimized. It should be noted, however, that the optimal condition for a particular self-reinforced composite may be dependent on what property is considered to be the most important (for example, fatigue resistance or fracture toughness). Similarly, the rate of fiber heating and cooling and the dwell time at the process temperature will affect the resultant properties.

Figure 9:
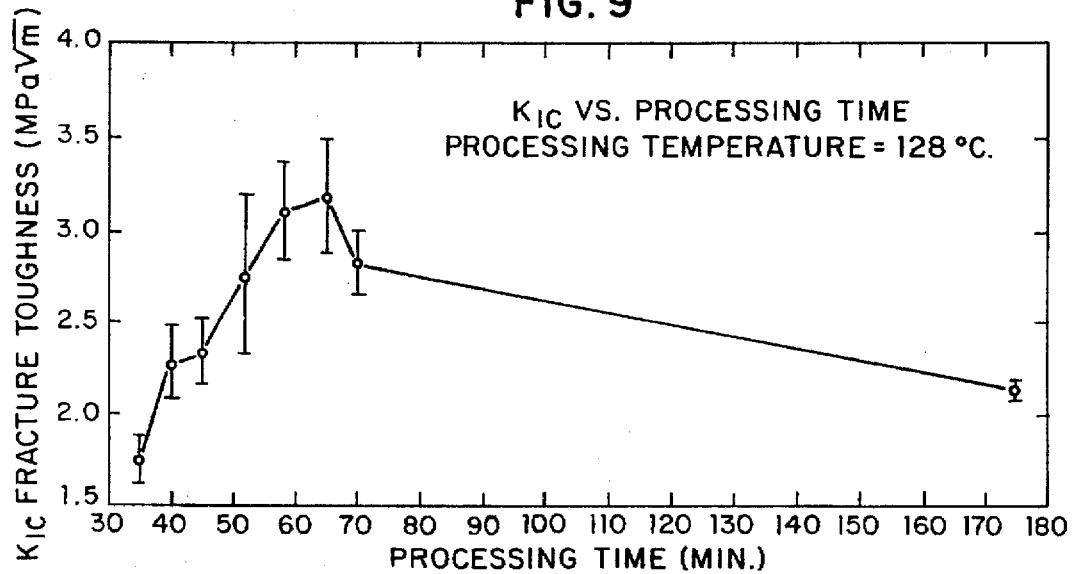
FIG. 9 is a graph depicting fracture toughness of a self-reinforced PMMA composite as a function of processing time for a fixed processing temperature and starting fiber material.

Exactly how orientation loss and fiber-fiber bonding are related to time is not entirely known, although the results of an experiment depicted in FIG. 9 are informative. In those experiments, the sintering temperature (128° C.), pressure (0.8 MPa), mold geometry, and amount and diameter of fiber were held constant and the time the samples remained in the oven was varied from 35 minutes up to 175 minutes. PMMA fibers made from 210,000 molecular weight polymer were used. The self-reinforced PMMA composite samples were made over this time range and the fracture toughness of the composites was evaluated. Also, the extent of molecular orientation of the fibers in such composites could be qualitatively assessed using a birefringent technique. That is, the composites were placed under cross polarized lenses and the amount of color present was used as an indication of the retained molecular orientation. The results of these experiments showed that the fracture toughness started low at 35 minutes (about 1.7 MPa√m) and increased to a maximum of about 3 MPa√m at 65 minutes. At longer times, the fracture toughness decreased and at 170 minutes the fracture toughness was about 2.2 MPa√m. The color observed in the cross polarized lenses indicated significant amounts of retained molecular orientation for times less than about 65 minutes. At 65 minutes and greater, the colorful birefringence was markedly diminished. These experiments show that there is an optimal processing time or range of times for the processing conditions (temperature, pressure, molecular weight, fiber diameter, composite thickness, mold geometry, heating method, etc.) to obtain the highest fracture toughness composite. For other mechanical properties such as fatigue or tensile strength, alternate optimal conditions may be required. Experiments were also carried out in which processing time and pressure were kept constant while processing temperature was changed and again, fracture toughness was measured. The results indicated that fracture toughness increases with increasing temperature and, while such data is incomplete, it is believed that fracture toughness reaches a maximum at some temperature and then slopes off at higher temperatures.

Figure 10:
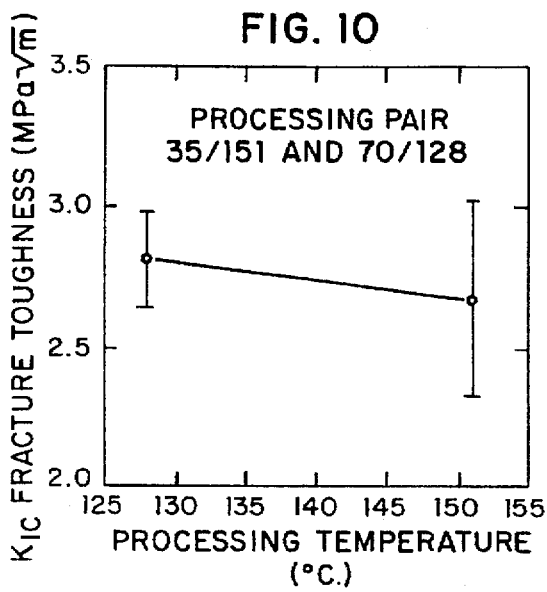
FIGS. 10 and 11 are graphs showing fracture toughness of a self-reinforced PMMA composite in relation to different combinations of processing times and temperatures.
Figure 11:
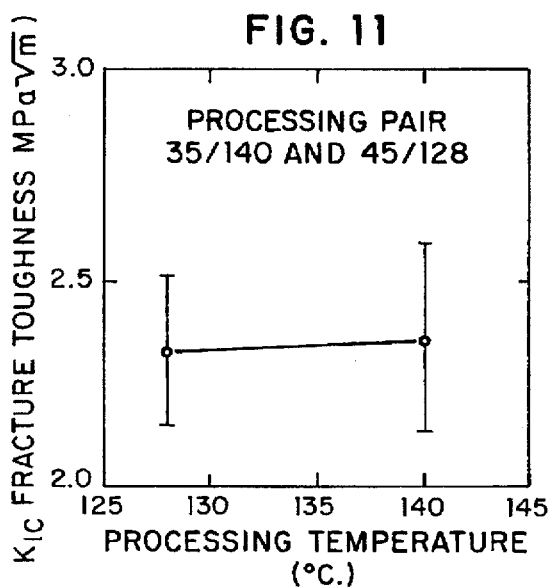

FIGS. 10 and 11 reveal that self-reinforced PMMA composites made in accordance with our process (in which heating and the application of pressure occur simultaneously between mold sections) may have similar fracture toughness characteristics even though they are produced by different combinations of sintering times and temperatures. In FIG. 10, the fracture toughness range for composites processed for 35 minutes at a temperature of 151° C. brackets the fracture toughness range for composites processed for 70 minutes at a temperature of 128° C. Similarly, in FIG. 11, the fracture toughness range for composites processed for 35 minutes at 140° C. encompasses the range for composites processed for 45 minutes at 128° C. In both graphs, a generally horizontal line connects the mean fracture toughness for each processing pair of composites.

The following examples further illustrate various aspects of this invention.

EXAMPLE 1

Two groups of test samples were prepared from unidirectional molecularly-oriented PMMA fibers sintered together, the samples of one group being formed from fibers of 40 μm diameter and those of the other from fibers of 120 μm diameter. The fibers were formed by melt extrusion accompanied by simultaneous drawing (at 170° C.) of the PMMA (167,000 weight average molecular weight) to produce fibers with longituindally-oriented molecular chains, the drawn length relaxation ratios of such fibers being approximately 15 to 18 for the 40 μm fibers and 11 to 15 for the 120 μm fibers. The fibers were then arranged in parallel into a room-temperature channel mold which was then clamped to a pressure of 3 to 8 atmospheres. Then the mold and fibers were placed in an oven at about 125° C. and left for about 25 minutes to sinter. After cooling, test samples measuring 20 mm by 10.5 mm by 2.5 mm were cut for evaluation of flexural strength and fracture toughness. Samples of similar size of Simplex-P bone cement (Howmedica, Inc., Rutherford, N.J.) and commercially-available PMMA sheet materials were also fabricated for comparison. A minimum of 5 samples of each material were prepared for three-point flexure tests and fracture toughness tests.

The three-point flexure tests and the fracture toughness tests were performed at a crosshead speed of 7.6 mm/min and 2.54 mm/min, respectively. In the fracture toughness tests, a single edge notched geometry was used and a pre-crack was imparted to the samples by way of a slow speed diamond saw, followed by cutting with a razor blade.

The results of the three-point flexure tests are presented in the following table:

| Three-Point Flexure Results (mean ± SD) | | | |
|---|---|---|---|
| Type of Material | Maximum Stress (MPa) | Modulus (GPa) | Elongation (%) |
| PMMA | 128.5 ± 11.4 | 2.67 ± 0.25 | 9.0 ± 1.3 |
| Simplex | 84.5 ± 5.2 | 2.63 ± 0.18 | 5.6 ± 0.8 |
| 120 μm | 118.4 ± 12.7 | 2.8 ± 0.12 | 35.3 ± 2.9 |
| 40 μm | 129 ± 14.0 | 2.75 ± 0.11 | 30.3 ± 4.9 |

In terms of bend strength, only the Simplex-P was statistically different from the other groups and there were no significant differences in modulus between groups. It will be noted, however, that the percent elongation was significantly greater for the samples composed of self-reinforced fibers than for the samples of PMMA and Simplex-P.

The fracture toughness test results are as follows:

| Fracture Toughness Results (mean ± SD) | |
|---|---|
| Type of Material | $K_{1c}$ (MPa√m) |
| PMMA | 1.28 ± 0.2 |
| Simplex-P | 1.27 ± 0.12 |
| 120 μm | 2.27 ± 0.54 |
| 40 μm | 3.17 ± 0.57 |

The comparative results also appear in bar graph form in FIG. 6. It can be seen that the fracture toughness values are significantly larger for the samples of self-reinforced PMMA fibers than for the Simplex-P and PMMA samples. Those samples composed of fibers of 40 μm had the highest fracture toughness values, nearly three times the fracture toughness for Simplex-P.

The differences in the data developed from these tests as revealed by the two tables and graph indicate that the self-reinforced composites were notably superior in resisting crack propagation (i.e., they were tougher, more fracture resistant). Optical and SEM evaluation of the fracture surfaces reveal that while the PMMA and Simplex-P samples had relatively smooth fracture surfaces perpendicular to the tensile stress axis, the self-reinforced composite samples showed significant crack splitting and branching in both tests. The fracture toughness results can therefore be explained by the crack branching and fiber splitting processes which divert the crack front and significantly increase the damage energy dissipated prior to failure.

EXAMPLE 2

Fourteen samples of each of four materials were prepared as described for the three point flexure test in Example 1. Each sample was thereafter subjected to three-point flexure as previously described except that an oscillatory loading at 5 Hz at an R ratio (minimum load over maximum load) of 0.1 was used to test each sample for flexural fatigue. Such flexural fatigue tests were performed in air and the data were used to generate maximum cyclic stress versus number of cycles to failure (S-N) curves.

During the flexural fatigue tests, several parameters were tracked over each test using computer data acquistion techniques. These included maximum deflection, modulus, and hysteretic energy loss per cycle. Such data were then used to assess the damage processes present.

Figure 7:
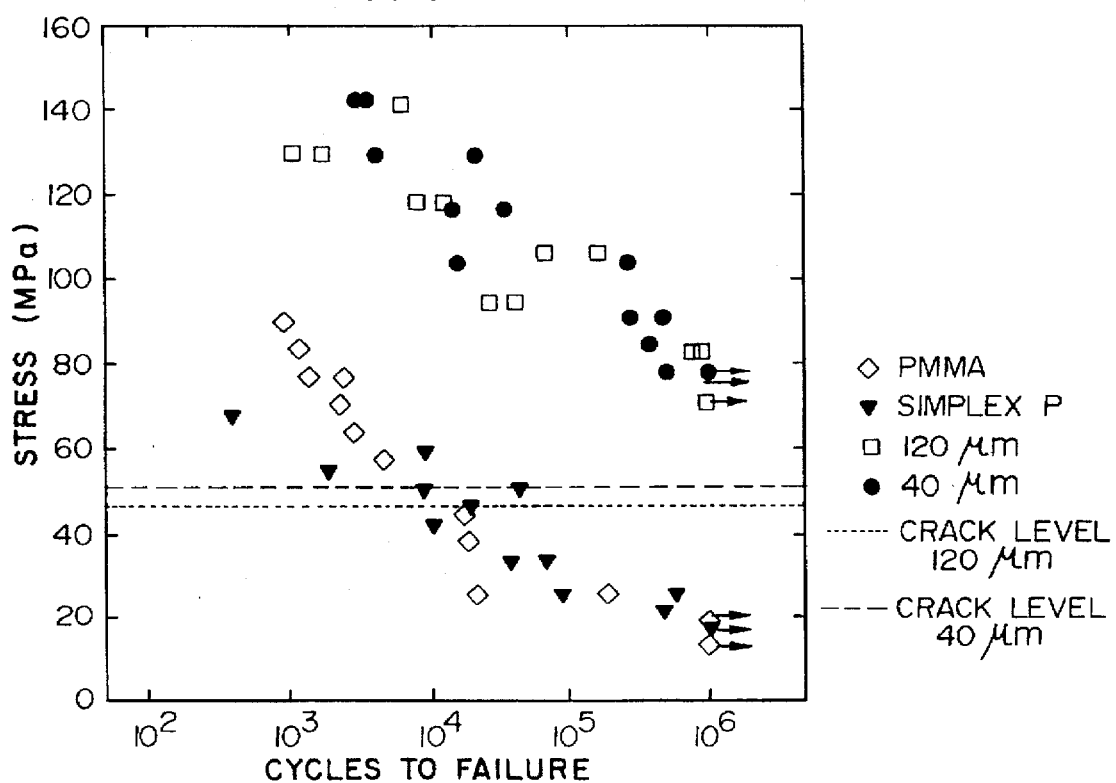
FIG. 7 is a plot depicting the results of flexural fatigue tests conducted on SRC-PMMA and other samples of the type described above.

The fatigue test results are shown in FIG. 7. This S-N curve shows that the fatigue strength for the self-reinforced fibrous samples of both sizes (fibers of 40 μm and 120 μm) was about 80 MPa at $10^6$ cycles, whereas the PMMA and Simplex-P samples had fatigue strengths of about 20 MPa. The self-reinforced fibrous samples therefore revealed about a four-fold improvement in fatigue resistance over the non-fibrous samples. Plots of the total hysteretic energy loss for each test showed that the total damage energy dissipated at 1,000,000 cycles was on the order of $10^3$J (Joules) for the fibrous samples while PMMA and Simplex-P only dissipated about 80J before failure.

For the reasons given in Example 1, the flexural fatigue results can be explained by the toughening of the composite and by crack branching and fibrous splitting processes for the fibrous samples, diverting the crack fronts and significantly increasing the damage energy dissipated prior to failure. That is further supported by the hysteretic energy loss versus cycles to failure for the fatigue tests which showed a much higher ability of the fibrous samples to absorb energy prior to failure.

EXAMPLE 3

Two woven fabrics composed of high strength PMMA fibers of 40 μm diameter and 120 μm diameter, respectively, for use in making self-reinforced preformed mantles for femoral prostheses in accordance with this invention, may be prepared as follows:

Pieces of commercially available PMMA (Cadillac Plastics, Inc.) of approximately $1.6 \times 10^5$ molecular weight are heated in an extruder to 169° C. by means of an electric heater and are extruded through a die at a constant rate with the extruded fiber being cooled in air (about 25° C.) and taken up on a drum located immediately adjacent the die's extrusion hole of selected diameter ($d_e$) at a draw velocity ($V_d$) substantially greater than the extrusion velocity ($V_e$). The fiber of 40 μm can be formed by drawing through a die having a die diameter $d_e$ of 0.1 cm at an extrusion velocity $V_e$ of 0.0254 cm/min and a draw velocity $V_d$ of 12 m/min to produce an oriented high-strength PMMA fiber having a length relaxation ratio of about 15 to 18. The 120 μm fiber can be formed by drawing through a die having a $d_e$ of 0.1 cm at a $V_e$ of 0.0254 cm/min and a $V_d$ of 5 m/min to produce an oriented high-strength PMMA fiber having a length relaxation ratio of about 11 to 15. The ultimate tensile strengths of such fibers are about 180 MPa for the 40 μm fiber and 120 MPa for the 120 μm fiber. Such procedures are essentially the same as used for preparing test samples composed of uni-directional 40 µm and 120 µm fibers as tested in Examples 1 and 2.

To facilitate further processing, the 40 µm fibers may then be formed into strands of 5 to 15 fibers each with one of the fibers wrapped about the remaining parallel fibers to maintain the integrity of the strand. Strands composed of 120 µm fibers are similarly formed with 5 to 10 fibers in each strand. The strands are then woven at right angles in an over-under pattern (or in any other suitable pattern) to produce two rolls or sheets of fabric, one being formed of woven strands composed of oriented high-strength 40 µm PMMA fibers and the other being formed of woven strands composed of oriented high-strength 120 µm PMMA fibers.

EXAMPLE 4

Femoral prostheses provided with self-reinforced mantles of oriented high-strength PMMA fibers woven into fabrics in accordance with Example 3 may be prepared as follows:

A woven fabric composed of 40 µm fibers prepared as in Example 3 is wrapped tightly about the stem of a metal (Vitallium) femoral prosthesis with the fibers at the commencement of the wrapping extending longitudinally and transversely to the main (longitudinal) axis of the stem. As wrapping is continued to produce multiple layers, the taper of the stem results in angular displacement of the fibers of successive layers with respect to the stem's axis, resulting in a quasi-isotropic orientation of the fibers when the wrapping is completed, at which time the thickness of the pre-mantle is approximately 2.5 mm and the number of layers in the wrapping is approximately 8 to 12. The layers are temporarily held in place by further processing, and the femoral prosthesis with the pre-mantle wrapped about its stem is sealed in a vacuum bag which is then placed in a heating chamber (autoclave). A vacuum of 2 to 3 atmospheres is applied in the bag and the chamber and its contents are heated at a temperature of 125° C. for 20 to 25 minutes. The completed femoral prosthesis with its sintered fibrous mantle contracted tightly about the stem and with the fibers retaining most of their original molecular orientation but now interlocked together, is then removed from the chamber and vacuum bag.

The same procedure is followed in making a femoral prosthesis with a PMMA mantle composed of a fabric wrapping of 120 µm fibers except that a lesser number of layers (approximately 6 to 8) is required to provide the same total thickness of 2.5 mm.

EXAMPLE 5

PMMA spun into 30 µm fibers with 212,000 molecular weight material using a draw temperature of 260° C. was used to fabricate unidirectional rods of self-reinforced composite. Fibers drawn at this temperature were found to have a strength of 200 MPa, a ductility of about 30% and a modulus of about 6 GPa. Without using a mold, approximately 14,000 fibers were wrapped about two spaced posts of a rigid frame and unidirectionally aligned. Then more fibers (approximately 500 fibers per centimeter of rod length) were spirally wrapped about the longitudinally oriented fibers to encase them and to constrain them into a cylindrical shape of circular cross section (i.e., a rod). This preform was then placed directly into a heated oven and was allowed to heat for between 5 and 10 minutes at 136° C. Afterwards, the preform was removed from the oven. During the heating, the fixed posts constrained the longitudinal fibers, preventing them from shrinking, while the circumferentially or spirally oriented fibers developed a shrinkage stress as they tried to heat relax. This shrinkage stress developed sufficient pressure on the longitudinally oriented fibers to force them to consolidate into a self-reinforced composite. The outer circumferential fibers were either kept in place or, depending on processing, they were able to be removed from the longitudinal fibers because they had not fully bonded to the longitudinal fibers. These rod-like unidirectional SRC-PMMA composite samples were then tested in flexure and were found to have a bending strength of about 145 MPa±20 MPa. The ductility of these samples was greater than 30%. The upper limit on ductility was not measured since no samples failed during testing; they just bent without fracture. The modulus of elasticity of these composites was 5.75 GPa±1.0 GPa. The properties of the composite are slightly less than those of the constituent fibers yet close enough to demonstrate that bonding of the fibers can be achieved with little loss in molecular orientation.

EXAMPLE 6

Fibers of polycarbonate (PC) can be melt spun into high strength fibers using the same transient temperature drawing process used for PMMA in Example 1. The specific temperatures and molecular weights for these fiber processes have not been optimized, however, fibers have been fabricated with melt temperatures ranging from 150° C. to 260° C. with good melt spinning (melt-extruding and drawing with simultaneous cooling) occurring around 180° to 210° C. Fibers of different diameters were drawn using the same polymer molecular weight and melt temperature. Similar heat relaxation ratio relationships as those seen with PMMA were obtained, such ratios ranging from about 3 to 1 to about 23 to 1 depending on fiber diameter. As the fiber diameter decreased, higher amounts of molecular orientation (and higher relaxation ratios) were obtained. The highest orientations were found in fibers of approximately 10 µm in diameter. The mechanical properties also showed significant increases with increasing orientation. The ultimate tensile strength increased to well over 1 GPa for fibers in the 10 to 20 µm range, which is roughly 20 times greater strength than bulk behavior. Such fibers may then be formed into a mat or tow and sintered at controlled times, pressures and temperatures as described in making self-reinforced composites of PMMA and other amorphous thermoplastics.

EXAMPLE 7

Polysulfone (PS) fibers were also fabricated and showed similar behavior to PC and PMMA fibers. That is, they showed variations in heat relaxation ratio with fiber diameter and significant increases in mechanical properties in particular, ultimate tensile strength. Heat relaxation ratios in the range of about 5 to 28 were obtained depending on fiber diameter, with the fibers of smaller diameter (approximately 30 µm) showing the greatest molecular orientation and tensile strength. The temperature needed to draw PS was greater than required for PMMA or PC (approximately 210° to 250° C.) because of the higher glass transition temperature for such fibers (about 190° C. as compared to 140° C. for PC and 105° C. for PMMA). Again, using controlled times, temperatures, and pressures, samples of PS fibers in matted form may then be formed into self-reinforced composites using procedures similar to those already described.

EXAMPLE 8

Approximately 14,000 PMMA fibers (30 µm in diameter) were prepared as in Example 5 and were similarly wrapped about two fixed parallel rods of a rigid frame (spaced about 15 cm apart) in a unidirectional orientation. The frame and wrapping was then preheated to a temperature of 140° C. for 3 to 5 minutes. Thereafter, the heated fibers extending between the posts were clamped into the channel of a mold that had been preheated to 140° C. and pressurized in the channel by a metal press bar for a period of 10 minutes. The samples were then cooled in air and when removed from the mold were found fully consolidated and highly birefringent.

In the procedure of this example, heating of the fibers was commenced prior to compressing or pressurizing the multiplicity of fibers that constitute the preform. This contrasts with a procedure in which the fiberous preform and mold are heated simultaneously and such heating commences only after the preform is positioned within the mold (see Example 1). The heating of the preform prior to pressurization, and the preheating of the mold prior to the pressurizing step, greatly reduces the duration of the molding operation (i.e., the time interval in which the composite is heated at sintering temperatures in the mold cavity).

While in the foregoing we have disclosed embodiments of this invention in considerable detail for purposes of illustration, it will be understood by those skilled in the art that many of these details may be varied without departing from the spirit and scope of the invention.

We claim:

1. A method of encasing a bone-implantable element of a joint prosthesis in a fatigue-resistant high-strength polymeric mantle bondable with acrylic bone cements, comprising the steps of melt-extruding and simultaneously drawing and cooling PMMA to produce fibers with longitudinally-oriented molecular chains in which each fiber has a diameter within the range of about 5 to 500 µm and a heat relaxation ratio of no less than about 3 to 1 in length; then wrapping said implantable element of said prosthesis with said fibers, or with a fabric formed of said fibers, to provide a pre-mantle of oriented fibers about said element; and thereafter sintering the fibers of said pre-mantle to contract and interlock the same together, while maintaining at least some longitudinal molecular orientation thereof, to provide a high-strength integrated mantle of connected, contracted, and oriented PMMA fibers.

2. The method of claim 1 in which there is the further step, prior to said wrapping step, of arranging said fibers into strands each containing from 2 to 1000 fibers; and thereafter weaving said strands together to form said fabric.

3. The method of claim 2 in which each of said strands contains from 10 to 200 fibers.

4. The method of claim 2 in which each of said strands contains from 25 to 150 fibers.

5. The method of claim 2 in which said fabric is wrapped in multiple layers about said implantable element of said prosthesis to provide said pre-mantle.

6. The method of claim 5 in which said mantle, following said sintering step, has an average thickness within the range of about 1 to 4 mm.

7. The method of claim 6 in which said average thickness is 2 to 3 mm.

8. The method of claims 1, 2 or 5 in which said fibers, following said steps of melt-extruding and simultaneously drawing and cooling, have a heat relaxation ratio of no less than about 6 to 1 in length prior to said sintering step.

9. The method of claim 1 in which there are the steps, prior to said melt extruding, of heating and mixing PMMA to extrusion temperatures with a minor percentage by weight of a uniformly dispersed finely-divided additive having particle sizes smaller than the diameter of said fibers when drawn and cooled.

10. The method of claim 9 in which said additive is a coloring or x-ray opacity-providing agent.

11. The method of claim 10 in which said additive is barium sulfate of a particle size within the range of about 1 to 15 µm.

12. The method of claim 1 in which said fibers of said wrapping are longitudinally oriented in pre-selected directions.

13. The method of claim 1 in which said fibers of said wrapping are randomly oriented.

14. A method for making a self-reinforced composite of an amorphous thermoplastic material comprising the steps of melt-extruding and simultaneously drawing and cooling an amorphous thermoplastic material consisting essentially of poly(methylmethacrylate) to produce fibers with longitudinally-oriented molecular chains in which each fiber has a diameter within the range of about 5 to about 500 µm and a heat relaxation ratio no less than about 3 to 1 in length; arranging said fibers to form an aggregation of fibers in which adjacent fibers are in contact with each other; and thereafter heating said aggregation of fibers to a temperature above the glass transition temperature of said material and below its degradation temperature, and applying pressure thereto, to soften and fuse together the outer surfaces of said fibers while maintaining at least some of the longitudinal orientation of the molecules of said material within said fibers.

15. The method of claim 14 which said steps of heating and applying pressure are simultaneous and coextensive in duration.

16. The method of claim 14 in which said steps of heating said aggregation of fibers commences prior to the application of pressure to said aggregation of fibers, and in which said fibers of said aggregation are constrained against longitudinal contraction during said steps of heating and applying pressure.

17. The method of claims 14, 15 or 16 in which each of said fibers prior to said heating step has a heat relaxation ratio of no less than about 6 to 1 in length.

18. The method of claim 14 in which there are the steps, prior to said melt extruding, of heating and mixing PMMA to extrusion temperatures with a minor percentage by weight of a uniformly dispersed finely-divided additive having particles sizes smaller than the diameter of said fibers when drawn and cooled.

19. The method of claim 18 in which said additive is a coloring or x-ray opacity-providing agent.

20. The method of claim 19 in which said additive is barium sulfate of a particle size within the range of about 1 to 15 µm.

21. A method for making a self-reinforced composite of an amorphous thermoplastic material comprising the steps of melt-extruding and simultaneously drawing and cooling an amorphous thermoplastic material consisting essentially of polycarbonate to produce fibers with longitudinally-oriented molecular chains in which each fiber has a diameter within the range of about 5 to about 500 µm and a heat relaxation ratio no less than about 3 to 1 in length; arranging said fibers to form an aggregation of fibers in which adjacent fibers are in contact with each other; and thereafter heating said aggregation of fibers to a temperature above the glass transition temperature of said material and below its degradation temperature, and applying pressure thereto, to soften and fuse together the outer surfaces of said fibers while maintaining at least some of the longitudinal orientation of the molecules of said material within said fibers.

22. A method for making a self-reinforced composite of an amorphous thermoplastic material comprising the steps of melt-extruding and simultaneously drawing and cooling an amorphous thermoplastic material consisting essentially of polysulfone to produce fibers with longitudinally-oriented molecular chains in which each fiber has a diameter within the range of about 5 to about 500 μm and a heat relaxation ratio no less than about 3 to 1 in length; arranging said fibers to form an aggregation of fibers in which adjacent fibers are in contact with each other; and thereafter heating said aggregation of fibers to a temperature above the glass transition temperature of said material and below its degradation temperature, and applying pressure thereto, to soften and fuse together the outer surfaces of said fibers while maintaining at least some of the longitudinal orientation of the molecules of said material within said fibers.

23. The method of claim 21 in which said steps of heating and applying pressure are simultaneous and coextensive in duration.

24. The method of claim 21 in which said steps of heating said aggregation of fibers commences prior to the application of pressure to said aggregation of fibers, and in which said fibers of said aggregation are constrained against longidutinal contraction during said steps of heating and applying pressure.

25. The method of claims 21, 23 or 24 in which each of said fibers prior to said heating step has a heat relaxation ratio of no less than 6 to 1 in length.

26. The method of claim 21 in which there are the steps, prior to said melt extruding, of heating and mixing PMMA to extrusion temperatures with a minor percentage by weight of a uniformly dispersed finely-divided additive having particle sizes smaller than the diameter of said fibers when drawn and cooled.

27. The method of claim 26 in which said additive is a coloring or x-ray opacity-providing agent.

28. The method of claim 27 in which said additive is barium sulfate of a particle size within the range of about 1 to 15 μm.

29. The method of claim 22 in which said steps of heating and applying pressure are simultaneous and coextensive in duration.

30. The method of claim 22 in which said steps of heating said aggregation of fibers commences prior to the application of pressure to said aggregation of fibers, and in which said fibers of said aggregation are constrained against longitudinal contraction during said steps of heating and applying pressure.

31. The method of claims 22, 29 or 30 in which each of said fibers prior to said heating step has a heat relaxation ratio of no less than about 6 to 1 in length.

32. The method of claim 22 in which there are the steps, prior to said melt extruding, of heating and mixing PMMA to extrusion temperatures with a minor percentage by weight of a uniformly dispersed finely-divided additive having particle sizes smaller than the diameter of said fibers when drawn and cooled.

33. The method of claim 32 in which said additive is a coloring or x-ray opacity-providing agent.

34. The method of claim 33 in which said additive is barium sulfate of a particle size within the range of about 1 to 15 μm.

* * * * *